United States Patent [19]

Hirdes

[11] Patent Number: 4,915,627

[45] Date of Patent: Apr. 10, 1990

[54] MATRIX CLAMP FOR DENTISTRY

[76] Inventor: Ruediger Hirdes, Kleinherbeder Str. 9a, D-5810 Witten, Fed. Rep. of Germany

[21] Appl. No.: 335,944

[22] Filed: Apr. 10, 1989

[30] Foreign Application Priority Data

Apr. 8, 1988 [DE] Fed. Rep. of Germany ....... 3811753

[51] Int. Cl.⁴ .............................................. A61C 5/04
[52] U.S. Cl. .................................................... 433/155
[58] Field of Search ................ 433/154, 155, 156, 157

[56] References Cited

U.S. PATENT DOCUMENTS 3,516,162  6/1970  Ainsworth .......................... 433/155
3,613,245  10/1971  Knight ................................ 433/155

Primary Examiner—Robert Peshock
Attorney, Agent, or Firm—Michael J. Striker

[57] ABSTRACT

A matrix clamp for dentistry comprises a frame, a threaded rod screwingly displaceable in the frame and having a front end and a rear end, a coulisse block arranged to releasably hold ends of a loop of a matrix band having an adjustable width, the coulisse block being slidingly displaceable by the front end of the threaded rod, a screw element having an inner thread, the rear end of the threaded rod being provided with an outer thread engaging with the inner thread of the screw element provided with a handle, the screw element being formed as a quick tensioning nut which is tiltable relative to a longitudinal axis of the threaded rod, and a tightening spring held on the threaded rod and acting upon the quick tightening nut.

38 Claims, 4 Drawing Sheets

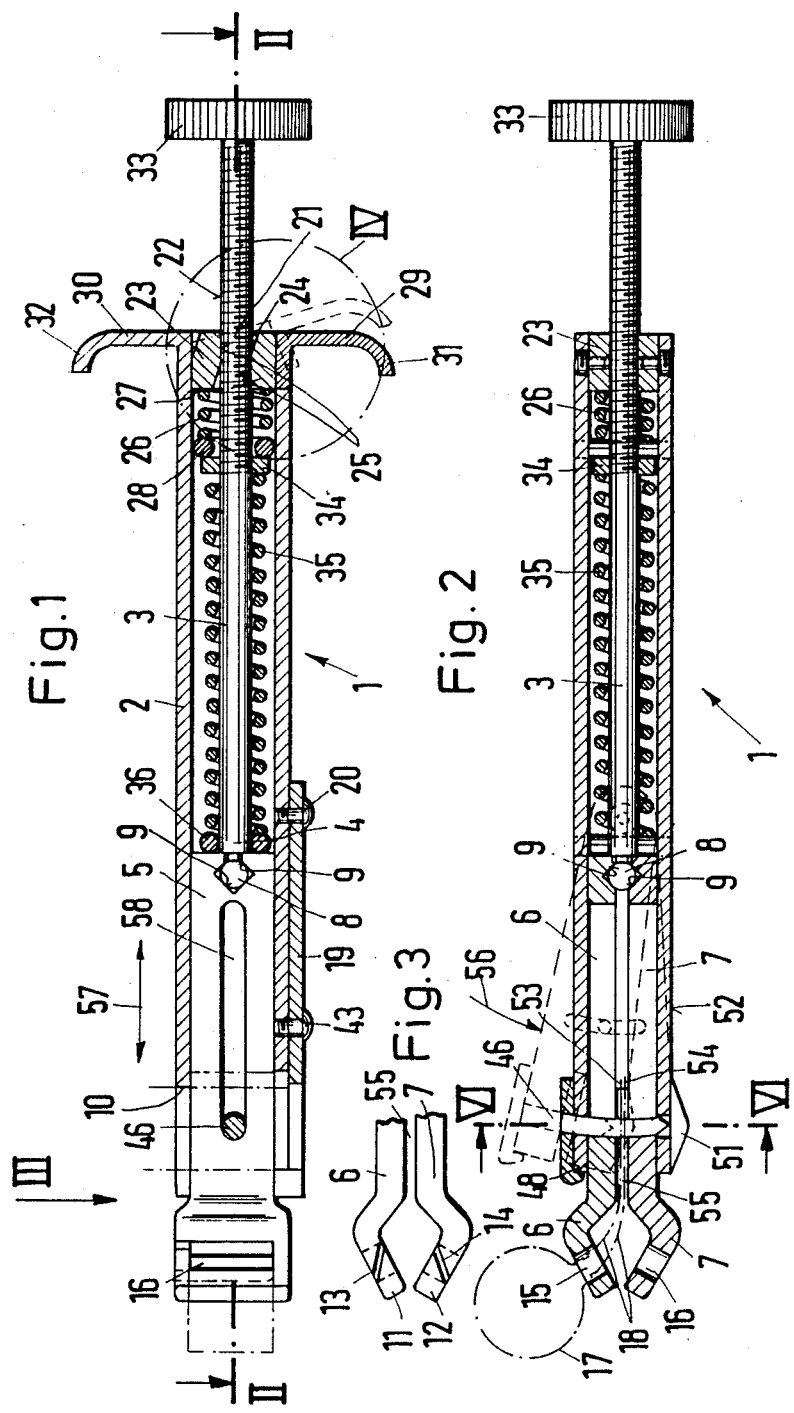

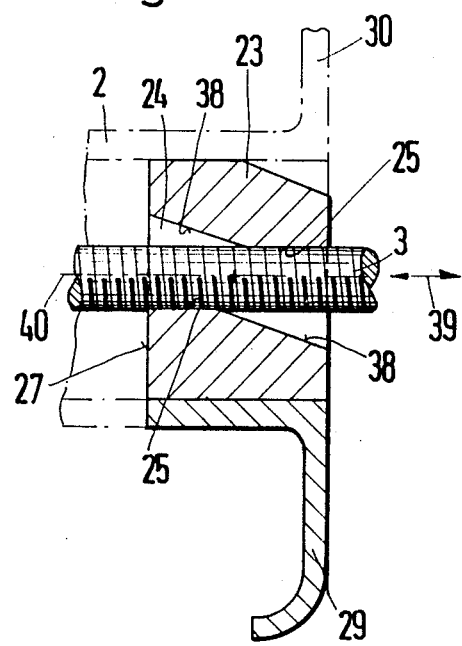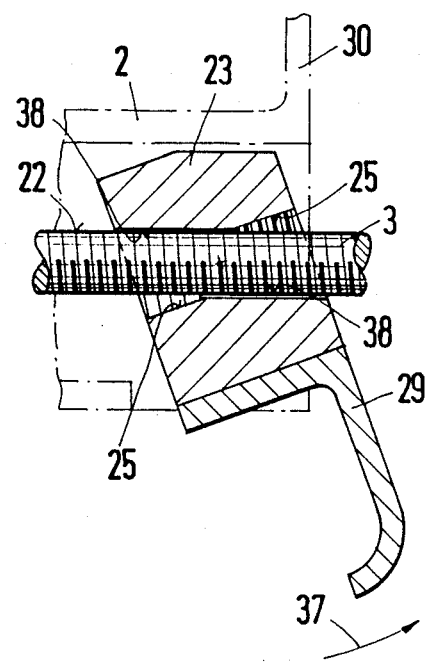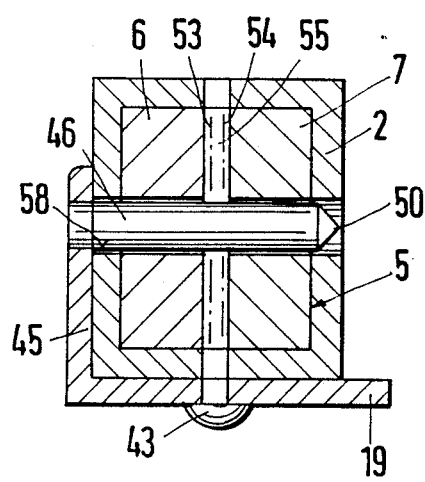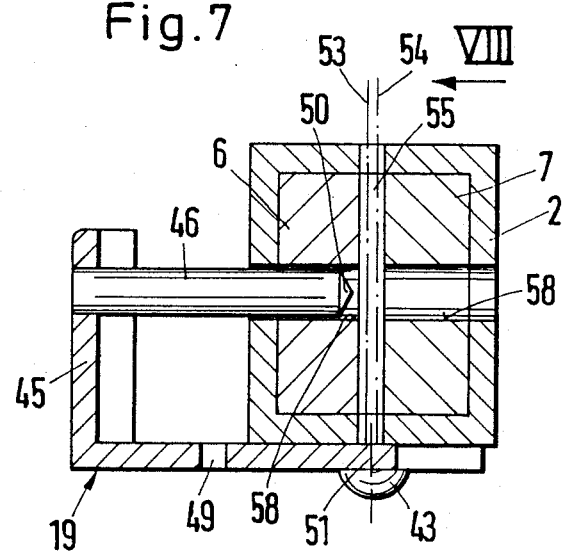

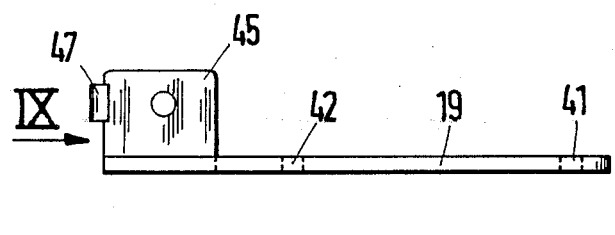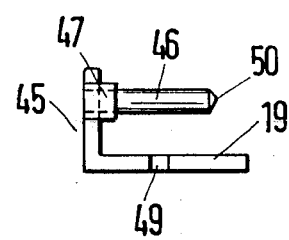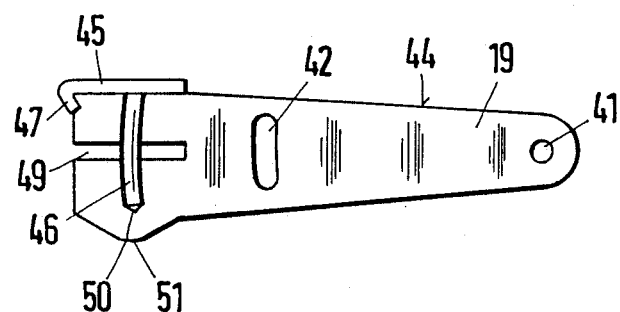

MATRIX CLAMP FOR DENTISTRY

BACKGROUND OF THE INVENTION

The present invention relates to a matrix clamp for dentistry.

More particularly, it relates to such a matrix clamp which has a threaded rod which is displaceable in a frame in a screw fashion, a coulisse block which is slidingly guided over the frame by the front end of the threaded rod and releasably holds by guiding slots the ends of a width-adjustable loop of a matrix band, and a screw element having an inner thread which engages an outer thread of the rear end of the threaded rod, wherein the rear end of the threaded rod is provided with a knurled handle.

In a matrix clamp of this type which is well known from frequent use, the guiding slot for engaging of the matrix band which is adjustable as to its width to form a loop is arranged at the front end of the frame. The ends of the matrix band are clamped in the front end of the threaded rod and the coulisse block. The coulisse block has a substantially U-shaped cross-section and guided by means of a rivet in a longitudinal hole of the frame. The rear end of the frame is bent in a U-shaped fashion and engaged by the threaded rod in an opening. The free fork-end of the frame engages an outer groove of a knurled nut as a screw element in a form-locking manner. The rear end of the threaded rod is provided with a knurled handle. The clamping and releasing of the free end of the matrix band between the front end of the threaded rod and the coulisse block can be performed by the knurled handle. By means of the knurled nut, the threaded rod and thereby the coulisse block and the free end of the matrix band can move in both longitudinal directions of the frame. The dentist presses down with the finger or thumb of its hand the matrix band applied around the tooth, while with his other hand he has to perform the time consuming screwing work for the matching narrowing of the loop of the matrix band. This screwing work cannot be eliminated even when the thread of the threaded rod formed as fine thread can be replaced with a thread of greater pitch. The reason is that for fine tightening of the matrix band to the configuration of a tooth to be treated, a fine adjustment in form of a fine thread is required.

In a further matrix clamp of this type known as Toffelmire, the coulisse block is composed of a parallelepiped-shaped body with an inclined slot for clamping the ends of the matrix band by the front end of the threaded rod engaging in the slot. In this matrix clamp the coulisse block has a dove-tail guide and is arranged slidingly on a frame rod provided with a corresponding cross-section. The front end of the frame is bent and provided with three different U-shaped guiding slots for guiding the matrix band.

The matrix band before the slots is shaped as a conical loop with an adjustable width and a configuration matching the teeth. In this case the matrix band is not formed as a regular band article, but instead is to be made as an individual item in form of a special band which due to its cutting assumes a conical shape during winding to the loop. In this matrix clamp a guiding slot is provided at both at the end side and at the left and right side of the front frame end. Also this matrix clamp possesses the disadvantage of a time consuming screwing work for narrowing and for expanding the matrix band applied on a tooth to be treated.

The last described matrix clamp possesses the disadvantage in that for resetting the matrix band from the left to the right position, the clamping between the end of the threaded rod and the respective coulisse block has to be released, then the band is reset and the clamping must be again produced. Since here the clamping is released in a positive fashion, therefore during conversion the clamp ends of the matrix band can slide between the clamping parts and must be then again inserted in a time consuming operation. As a result, damages to the matrix band are often unavoidable. The same is true with respect to the insertion and exchange of the matrix band. Further, in both matrix clamps the coulisse block is prescrewed in the front position in which it expands the loop of the matrix band. After placing the matrix band on a tooth to be treated, the respective coulisse block must be screwed back for narrowing the loop of the matrix band in a time consuming screwing operation.

Both above described matrix clamps operate under ergonomically unfavorable conditions in or in the immediate vicinity to the mouth opening of the patient. The reason is that the dentist must hold the matrix clamp with the fingers of one hand and simultaneously press down the matrix band onto the tooth, while with its indicating finger or thumb of another hand he must performing the screwing work for narrowing and expanding the loop of the matrix band.

SUMMARY OF THE INVENTION

Accordingly, it is an object of the present invention to provide a matrix clamp which avoids the disadvantages of the prior art.

More particularly, it is an object of the present invention to provide a matrix clamp of the above mentioned type with which ergonomically favorable handling for reducing and expanding the loop of the matrix band or a tooth to be treated can be performed in a time which is only a fraction of the time required with the known matrix clamps.

In keeping with these objects and with others which will become apparent hereinafter, one feature of the present invention resides, briefly stated, in a matrix clamp in which a screw element is formed as a quick tightening nut tiltable relative to the longitudinal axis of the threaded rod and located under the action of a tightening spring which holds the quick tightening nut in a clamping position with a threaded rod.

Due to this construction in accordance with the present invention, the time consuming screwing work for expanding or narrowing the loop of the matrix band is dispensed with. The reason is that with one movement the quick tightening nut is tilted and simultaneously the threaded rod is displaced through the threaded opening to the desired loop width and then released. Then the quick tightening nut is tilted back under the action of the tightening spring to its clamping position. Then the dentist assures the fixing of the loop of the matrix band by the knurled handle of the threaded rod with a short blocking turning angle. The whole process takes only one or two seconds and performed in an ergonomically favorable manner since the tilting of the threaded nut and the displacement of the threaded rod can be performed in one working step by one hand similarly to the handling of a syringe, for example with indicating finger, middle finger and thumb of one hand.

The tightening spring for the quick tightening nut supports advantageously with its one end against an arresting surface of the quick tightening nut arranged concentrically on the threaded rod. Its another end abuts against a stationary projection of the frame. The tightening spring can be formed as a helical spring or conical spring arranged concentrically around the threaded rod, it also can be formed as a plate spring or leaf spring.

In accordance with a further advantageous embodiment of the invention, the quick tightening nut is provided with an ergonomically favorable projection extending beyond the outer contour of the frame. At the height of the projection of the quick tightening nut, the frame is provided with an ergonomically favorable projecting holding element. It determines with the above mentioned projection of the quick tightening nut a gripping favorable position. The holding element and the projection of the quick tensioning nut have a rounded edge region, and in connection with the knurled handle at the rear end of the threaded rod are formed similarly to a syringe.

In contrast to the prior art, the guiding slots for the width-adjustable loop of the matrix band are provided at the free end of the coulisse block, and no longer on the frame. Thereby during displacement of the threaded rod the coulisse block is pre-displaced and correspondingly the loop of the matrix band extending from the guiding slot is reduced. during a return pulling of the threaded rod and thereby the coulisse block, is respectively expanded.

The application of the new matrix clamp and its ergonomic features are also improved by the fact that the guiding slots have a conical, wedge-like or cylindrical shape, and provided with a narrower insertion slot on the upper and/or lower side of the coulisse block. Since the matrix band due to its elasticity has a tendency after its insertion into guiding slot to expand to a loop, the side surfaces of the loop lie very tightly on the side walls of the guiding slot and cannot slide from the considerably narrower insertion slot of the coulisse block.

In accordance with an advantageous embodiment of the invention, the coulisse block is formed as one-part element or composed of several parts, and in each case is provided with an axis-symmetrical longitudinal slot extending substantially in an axial direction of the longitudinal axis of the threaded rod. The slot is used for insertion of the matrix band which is releasably held at this point. The ends of the matrix band are turnably supported or held in the longitudinal slot on a plug. The plug is arrestable in the frame and engages with the matrix band. It is mounted on a side wall of a bottom plate turnably supported on the lower side of the frame. The bottom plate is arrestable on the frame through an arresting projection. In this advantageous embodiment the compressed ends of a matrix band can be inserted in an ergonomically simple manner for example a dentist aid through the axis-symmetrical longitudinal slot of the coulisse block to abutment against the bottom plate. Then the bottom plate is turned with its side wall to the arresting position. Thereby, simultaneously the block form-lockingly engages both ends of the matrix band and simultaneously forms a pivot for the matrix band for resetting from one guiding slot into another guiding slot. Due to this construction it is not necessary to release a clamping in contrast to the prior art. It is now sufficient to narrow the loop for guiding the same from the insertion slot, then turn it from the insertion slot on the plug which acts as a pivot, then to insert it in the insertion slot of another guiding slot. This process with its simple handling and speed no longer can be compared with the time consuming puzzle-like operation and possible damages to the matrix clamp in accordance with the prior art.

In accordance with a further embodiment of the present invention, the bottom plate is provided with a radial slot at a distance from the pivot axis. A rivet or screw pin which forms a limit for the turning and mounted on the frame can expand through the radial slot. The coulisse block has a longitudinal hole extending parallel to the longitudinal axis of the threaded rod for the plug. At its end which faces the threaded rod it is coupled with the plug in a form-locking and displaceable manner through a ball.

In accordance with another embodiment of the present invention, the arresting of the bottom plate and thereby the plug can be easily released, and the abutment limit can be provided for the ends of the matrix band inserted in the longitudinal slot of the coulisse block. For this purpose the bottom plate on its side which is opposite to the plug holding side wall is provided with a side edge which extends beyond the free tipped end of the plug and engages the slot at this point. In the arrested position of the bottom plate the side edge overlaps associated side walls of the frame.

The coulisse block can be formed advantageously as a two-part element and displaced in a frame having a tubular cross-section. For easier stabilization and handling during compressing, the coulisse block can be composed of two parallelepiped-shaped coulisse halves guided on a frame with a rectangular or square cross-section It is, however also possible to provide the frame with a circular cross-section and the coulisse block with parts having each a semi-circular outer contour.

In the inventive matrix clamp the loop of the matrix band after finished tooth treatment can be released fast and in an ergonomically simple manner. This is achieved in that the coulisse block is displaceable against the force of further tightening spring to a front position for narrowing the loop of the matrix band. This tightening spring can be formed advantageously as a cylindrical helical spring concentrically surrounding the threaded rod. The front end can abut against a disc fixedly connected with the threaded rod, while its another end can abut against the projection of the frame in an inner space thereof. By after releasing of the fixation of the matrix band by a short angular turning of the handle, the quick tightening nut is tilted. Under the action of the pre-stressed tightening spring the threaded rod slides back with entraining of the coulisse block to the initial position to increase the width of the loop.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. I is a longitudinal section of a matrix clamp in accordance with the present invention;

FIG. 2 is a view showing a section taken along the line II—II in FIG. 1;

FIG. 3 is a partial plan view of a front end of a coulisse block of the inventive matrix clamp of FIG. 1;

FIG. 4 is an enlarged view of a partial section IV of FIG. 1 in a clamping position of a quick tightening nut of the inventive matrix clamp;

FIG. 5 is a view substantially corresponding to the view of FIG. 4, but showing the quick tightening nut in a tilted and therefore released position;

FIG. 6 is a view showing a section taken in direction of the line VI—VI in FIG. 2 with an arrested bottom plate of the inventive matrix clamp;

FIG. 7 is a view substantially correspond to the view of FIG. 6, but showing the unlocked and turned-off bottom plate;

FIG. 8 is a side view of the bottom plate in direction of the arrow VIII in FIG. 7;

FIG. 9 is a side view of FIG. 8 in direction of the arrow IX of FIG. 8;

FIG. 10 is a plan view of the bottom plate shown in FIG. 8 of the inventive matrix clamp.

DESCRIPTION OF THE PREFERRED EMBODIMENTS

Figure 11:
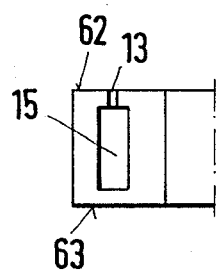
FIGS. 11–14 are views showing various shapes of a guiding slot of the coulisse block with a narrow insertion slot of the inventive matrix clamp.

A matrix clamp in accordance with the present invention is identified as a whole with reference numeral 1. As can be seen from FIGS. 1 and 2, it includes a tubular frame 2 with a rectangular cross-section, a screw movable threaded rod 3, and a two-part coulisse block 5 which is displaced by a front end 4 of the threaded rod 3 along the frame 2.

Both halves 6 and 7 of the coulisse block 5 are shown in FIG. 2. The threaded rod 3 has a ball 8 on its front end 4. The ball is engaged on its diametrically opposite sides by two recesses 9 of the halves 6 and 7 of the coulisse block. Since the coulisse block 5 is engaged with its both halves 6 and 7 up to approximately a front edge 10 of the tubular frame 2 from all sides, the halves 6 and 7 of the coulisse block are displaceably coupled with the ball 8 in a form-locking manner. The ball 8 forms a spherical joint with the recess 9 of the halves 6 and 7 of the coulisse block.

The free ends 11 and 12 of the halves 6 and 7 of the coulisse block are provided with inclined and relatively narrow insertion slots 13 and 14. They are also provided with greater guiding slots which are located directly underneath the insertion slots 13 and 14. They serve for receiving a loop 17 of a matrix band 18. Loop 17 is shown in a dash-dot line and has an adjustable width.

The lower side of the frame 2 in the region of the coulisse block 5 is engaged from below by a bottom plate 19. The bottom plate 19 is mounted on a frame 2 pivotally through a pivot pin 20. The bottom plate 19 will be described in detail hereinbelow.

The threaded rod 3 engages with its rear end 21 having an outer thread 22 in an inner thread 25 of an opening 24 in a quick tightening nut 23. The quick tightening nut 23 is arranged under the action of a tightening spring 26. In the clamping position shown in FIG. 1, the tightening spring 26 is held by the threaded rod 3.

The tightening spring 26 is supported with its one end against an end surface of a quick tightening nut 23 which concentrically surrounds the threaded rod 3. The other end of the tightening spring 26 is supported on a stationary bracket-shaped projection 28 which is mounted stationarily on the frame 2.

In the shown example the tightening spring 26 is formed as a helical spring which concentrically surrounds the threaded rod 3. It is however also possible to form the tightening spring 26 as a conical spring, a plate spring or a leaf spring.

The quick tightening nut 23 is provided with an ergonomically favorable projection 29 which extends outwardly beyond the outer contour of the frame 2. At the height of the projection 29 of the quick tightening unit 23, the frame 2 has a similarly ergonomically favorable spring-biased holding element 30. The holding element 30 and the projection 29 of the quick tightening nut 23 have rounded edge regions 31 and 32. The edge region together with a knurled handle 33 provided on the rear end of the threaded rod 3 are formed as a syringe. A disc 34 is located at a side which is opposite to the tensioning spring 26 behind the stationary projection 28. The disc 34 is connected with the threaded rod 3 for joint rotation therewith and serves for supporting the projection 28. A helical spring formed as a cylindrical helical spring and concentrically surrounding the threaded rod 3 abuts against the disc 34. The helical spring 35 is held with its another end by a bracket-shaped projection 36 which is stationarily connected with the frame 2.

The operation of the quick tightening nut 23 in connection with the threaded rod 3 is illustrated in FIGS. 4 and 5. In the position shown in FIG. 4, the outer thread 22 of the threaded rod 3 engages in the inner thread 25 of the quick tightening nut 23. In this position the threaded rod 3 can be rotated by the knurled handle 33 and thereby moved inside the quick tightening nut 23 over the threads 22, 25 similarly to a screw.

In the position shown in FIG. 5 the quick tightening nut 23 is tilted by the projection 29 in direction of the arrow 37, and thereby the inner thread 25 of the quick tightening nut 23 disengages from the outer thread 22 of the threaded rod 3. The outer thread 22 of the threaded rod 3 abuts against a threadless surface 38 of the quick tightening nut 23. Thereby the threaded rod 3 can be quickly displaced in both direction of the double arrow 39. When the operator releases the quick tightening nut 23, it is tilted under the action of the tightening spring 26 to the position shown in FIG. 4. Thereby again its inner thread 25 comes to engagement with the respective outer thread 22 of the threaded rod 3. After this, the threaded rod 3 can displace only by rotation of the knurled handle 33 in both directions of the double arrow 39 similarly to a screw.

The tilting movement of the quick tightening nut 23 is always performed relative to the longitudinal axis 40 of the threaded rod 3.

FIGS. 8–10 show the bottom plate 19 on three views. It is provided with a radial slot 42 at a distance from a throughgoing opening 41 for the pivot axle 20. A rivet pin or a screw pin 43 mounted on the frame 2 extends through the radial slot 42 and serves for limiting the turning movement, as can be seen from FIG. 1.

The bottom plate 19 has a side edge 44 with a somewhat perpendicularly upstanding side wall 45. A plug 46 is stationarily arranged in the center of the side wall 45. The side wall 45 has an arresting projection 47 which arrestingly interengages with a correspondingly formed arresting surface 48 on the associated side of the frame 2, as shown in FIG. 2. Thereby the bottom plate 19 can be arrested in the position shown in FIG. 2, and after releasing of this arresting can be turned to the position which is shown in FIG. 2 in a broken line, to the extent permitted by the parts which form a limit for turning, namely the slot 42 and the pin 43.

As can be seen from FIG. 10 the bottom plate at the height of the plug 46 is provided with a slot 49 and a side edge 51 which extends over a free tipped end 50 of the plug 46. The side edge 51 extends beyond the associated side wall 52 in the arrested position of the bottom plate 19 as shown in FIG. 2. This projecting side edge 51 of the bottom plate 19 performs two functions. On the one hand, it effects in a simple manner the release of the arresting performed by the parts 47, 48 of the side wall 45 by applying a pressure in direction to the associated side wall 52 of the frame. On the other hand, the projecting side edge 51 engages a longitudinal slot 55 between both halves 6 and 7 of the coulisse block when the bottom plate 19 is turned to a position fixed by the turning limiting parts 42, 43 and shown in a broken line in FIG. 2. In this position the tip 50 of the pin 46 is withdrawn from the longitudinal slot 55 between the halves 6 and 7 of the coulisse block, so that the ends 53, 54 of the matrix band 18 are inserted from above (see FIG. 7) into the slot 55 til it abuts with the projecting side edge 51 against the bottom plate 19. Then the bottom plate 19 can be pressed from the position shown in a broken line in FIG. 2 to the position shown in solid line, in direction of the arrow 56 until it reaches its end position shown in FIG. 6. The tipped end 50 of the plug 46 perforates both ends 53, 54 of the matrix band 18 and forms a pivot for it. Therefore, when desired the loop 17 of the matrix band 18 can be inserted through the narrow insertion slot 13 of the half 6 of the coulisse block into the insertion slot 14 of the half 7 in the guiding slot 16. For this resetting of the matrix band 18, it is no longer necessary to release a clamping as in the prior art, since now the plug 46 functions as a pivot for the matrix band. Thereby the damages to the matrix band 18 which occurred in the prior art during resetting are prevented.

The above described turning in and turning out of the bottom plate 19 is explained hereinbelow with reference to FIGS. 6 and 7, wherein the parts which are common with those in FIGS. 1, 2 and 8-10 are identified with the same reference numeral. It can be seen from FIG. 6 that in the turned-in and arrested position of the bottom plate 19 with the plug 46, the ends 53, 54 of the matrix band 18 are held between both halves 6 and 7 of the coulisse block in a turnable manner.

As can be seen from FIG. 7, the ends 53 and 54 during insertion in the slot 55 abut against the side edge 51 which forms an abutment and overlaps the slot 55 at this position so as to cover the latter. It can also be seen in FIGS. 6 and 7 that the slot 49 of the bottom plate 19 in the closing position shown in FIG. 6 is located in alignment under the slot 55 between the halves 6 and 7 of the coulisse block.

The parts 6 and 7 of the coulisse block are provided each with an elongated opening 58 extending parallel to the longitudinal axis 40 of the threaded rod 3. They are provided for permitting the displacement of the parts 6 and 7 of the coulisse block in both directions of the double arrow 57 in FIG. 1, by the threaded rod 3, despite the plug 46 which intersects their displacement path.

The new matrix clamp 1 operates in the following manner:

In the position shown in FIGS. 1, 2 and 7, the ends 53, 54 of the matrix band 18 with the turned-off bottom plate 19 are inserted from above into the slot 55 seen in the section of FIG. 7 so far until they abut against the side edge 51 of the bottom plate 19 which serves as an abutment. After this, the bottom plate 19 is displaced to its arrested position in direction of the arrow 56 in FIG. 2 by applying a pressure against the side wall 45. Thereby the plug 46 which has a circular arc-shape turns with perforation of the ends 53, 54 of the matrix band 18 to its position shown in solid line in FIG. 2, which can be recognized on an enlarged side of FIG. 6. Then the loop 17 of the matrix band 18 is somewhat compressed on its loop end between two fingers of a hand, for example between the thumb and indicating finger, and selectively displaced through the insertion slot 13 of the part 6 of the coulisse block or through the insertion slot 14 of the part 7 of the coulisse block into the slots 15, 16 located underneath. After its release, the loop 17 expands under the action of its elasticity to the position shown in FIG. 2, and thereby can no longer slide out of the narrow insertion slots 13, 14. During this process, the plug 46 acts as a pivot. In this position, the coulisse block 5 or its parts 6, 7 assume the position shown in FIGS. 1 and 2.

Now in this position the matrix band which has its maximum loop width is displaced over a not shown tooth to be treated. For narrowing the width of the loop 17 of the matrix band 18, the quick tightening nut 23 is titled in the above described manner in accordance with FIGS. 1 and 5, and in this unlocked position the threaded rod 3 is momentarily displaceable for example by a thumb of one hand. Thereby the parts 6 and 7 of the coulisse block slide with their elongated openings 58 on the fixed plug 46 and therefore the width the loop 17 of the matrix band 18 is momentarily reduced. As long as traceable resistance is available, the projection 29 of the quick tightening nut 23 is released and assumes its arrested position shown in FIG. 4 under the action of the tightening spring 26. Immediately by rotation of the knurled handle 33 over a relatively small angle of rotation, the fine end position of the loop 17 around the respective tooth is adjusted. This whole process continues not longer than one or two seconds. In the prior art with the most skilled handling, at least seven to ten seconds were required.

This clamping of the loop 17 of the matrix band is performed with pre-tensioning of the tightening spring 35.

For releasing the matrix band 18 after the required tooth treatment, the loop 17 is again expanded. This is performed momentarily when again the quick tightening nut 23 is tilted to the position shown in FIGS. 1 and 5, thereby under the action of the tightening spring 35, the threaded rod 3 moves back fast with the coulisse block 5 to the position of FIG. 1. Therefore the loop 17 is positively expanded and can be lifted from the treated tooth. The exchange and the conversion of the matrix band 18 is performed after releasing the arresting 47, 48 of the bottom plate 19 in the manner described in connection with FIGS. 2, 6 and 7.

FIGS. 11-14 show different shapes of the guiding slots 15, 16 in the vicinity of the free ends 11, 12 of the halves 6, 7 of the coulisse block 5.

FIG. 11 shows the guiding slot 15 of rectangular shape which can be seen from FIGS. 1 and 3. Thereby a special cylindrical loop 17 of the matrix band 18 is produced.

Figure 12:
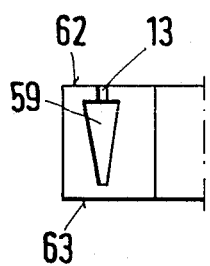

FIG. 12 shows the guiding slot 59 with a conical shape. Because of the elasticity of the matrix band 18, a conical shape of the loop 17 is obtained in a positive manner.

Figure 13:
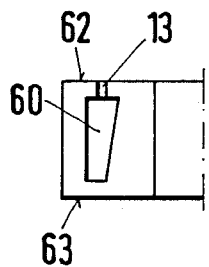
Figure 14:
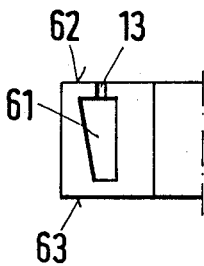

FIGS. 13 and 14 show different sides of wedge-shaped guiding slots 60 and 61. Due to this shape, the loop 17 obtains also a conical partial shape. On the upper side 62 of the parts 6 and 7 of the coulisse block 5, a respective insertion slot 13 and 14 extend inclinedly and forms considerably narrower. This insertion slot 13 or 14 can also be provided on the lower side 63 of the halves 6 and 7 of the coulisse block 5, with the exception of the embodiment of FIG. 12.

It will be understood that each of the elements described above, or two or more together, may also find a useful application in other types of constructions differing from the types described above.

While the invention has been illustrated and described as embodied in a matrix clamp for dentistry, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A matrix clamp for dentistry, comprising a frame; a threaded rod screwingly displaceable in said frame and having a front end and a rear end; a coulisse block arranged to releasably hold ends of a loop of a matrix band having an adjustable width, said coulisse block being slidingly displaceable by said front end of said threaded rod; a screw element having an inner thread, said rear end of said threaded rod being provided with an outer thread engaging with said inner thread of said screw element and also being provided with a handle, said screw element being formed as an axially immovable quick tensioning nut which is tiltable relative to a longitudinal axis of said threaded rod; and a tightening spring held on said threaded rod and acting upon said quick tightening nut.

2. A matrix clamp as defined in claim 1, wherein said handle is formed as a knurled handle.

3. A matrix clamp as defined in claim 1, wherein said quick tightening nut is arranged concentrically around said threaded rod.

4. A matrix clamp as defined in claim 1, wherein said quick tightening nut has an end surface; and further comprising a projection stationarily arranged on said frame, said tightening spring having one end abutting against said end surface of said quick tightening nut and another end abutting against said projection.

5. A matrix clamp as defined in claim 1, wherein said tightening spring is formed as a spring which concentrically surrounds said threaded rod.

6. A matrix clamp as defined in claim 5, wherein said tightening spring surrounding said threaded rod is formed as a helical spring.

7. A matrix clamp as defined in claim 5, wherein said tightening spring surrounding said threaded rod is formed as a conical spring.

8. A matrix clamp as defined in claim 1, wherein said tightening spring is formed as a plate spring.

9. A matrix clamp as defined in claim 1, wherein said tightening spring is formed as a leaf spring.

10. A matrix clamp as defined in claim 1, wherein said quick tightening nut is provided with an ergonomically favorable projection extending outwardly beyond an outer contour of said frame.

11. A matrix clamp as defined in claim 10, wherein said frame is provided with an ergonomically favorable holding element extending at the height of said projection of said quick tightening nut.

12. A matrix clamp as defined in claim 11, wherein said holding element and said projection of said quick tightening nut have rounded edge regions which in connection with said handle form a syringe-shaped unit.

13. A matrix clamp as defined in claim 1, wherein said coulisse block has a free end provided with a guiding slot for the loop of the matrix band.

14. A matrix clamp as defined in claim 13, wherein said guiding slot has a conical shape.

15. A matrix clamp as defined in claim 13, wherein said guiding slot has a wedge shape.

16. A matrix clamp as defined in claim 13, wherein said guiding slot has a cylindrical shape.

17. A matrix clamp as defined in claim 13, wherein said guiding slot has a narrower insertion slot provided on one of upper and lower sides of said coulisse block.

18. A matrix clamp as defined in claim 1, wherein said coulisse block is formed as a one-piece integral element.

19. A matrix clamp as defined in claim 1, wherein said coulisse block is composed of a plurality of individual parts.

20. A matrix clamp as defined in claim 1, wherein said coulisse block is provided with a longitudinal slot extending substantially in an axial direction of a longitudinal axis of said threaded rod for inserting a releasably held matrix band.

21. A matrix clamp as defined in claim 20; and further comprising a plug arrested on said frame and turnably holding ends of the matrix band in said longitudinal slot.

22. A matrix clamp as defined in claim 21; and further comprising a bottom plate which is externally supported on a lower side of said frame, and has a side wall, said plug being mounted on said side wall of said bottom plate.

23. A matrix clamp as defined in claim 22, wherein said frame has an arresting surface, said bottom plate having an arresting projection which is arrestable on said arresting surface of said frame.

24. A matrix clamp as defined in claim 22, wherein said bottom plate has a turning axis and is provided with a radial slot at a distance from said turning axis; and further comprising means for limiting the turning of said bottom plate and including a pin mounted on said frame and extending through said radial slot.

25. A matrix clamp as defined in claim 24, wherein said pin of said limiting means is formed as a rivet pin.

26. A matrix clamp as defined in claim 24, wherein said pin of said limiting means is formed as a screw pin.

27. A matrix clamp as defined in claim 21, wherein said coulisse block has a longitudinal hole extending parallel to a longitudinal axis of said threaded rod for engaging said plug, said coulisse block having an end which faces toward said threaded rod; and further comprising a ball which form-lockingly displaceably couples said end of said coulisse block with said plug.

28. A matrix clamp as defined in claim 22, wherein said plug has a free tipped end, said bottom plate having a side which is located opposite to said side wall and is provided with a side edge extending over said free tipped end of said plug, said frame having a side wall which is overlapped by said side edge in an arrested position of said bottom plate.

29. A matrix clamp as defined in claim 1, wherein said frame has a tubular contour, said coulisse block being composed of two parts and arranged displaceably in said frame.

30. A matrix clamp as defined in claim 1, wherein said frame has a four-cornered cross-section, said coulisse block being composed of two parallelepiped-shaped parts and guided in said frame.

31. A matrix clamp as defined in claim 30, wherein said frame has a rectangular cross-section.

32. A matrix clamp as defined in claim 30, wherein said frame has a square cross-section.

33. A matrix clamp as defined in claim 1; and further comprising a further tightening spring arranged so that said coulisse block is displaceable against the force of said further tightening spring to a front position in which the loop of the matrix band is narrowed.

34. A matrix clamp as defined in claim 33, wherein said further tightening spring is formed as a cylindrical helical spring which concentrically surrounds said threaded rod; and further comprising a disc mounted on said threaded rod for joint rotation therewith, and a projection provided on said frame, said further tightening spring having one end abutting against said disc and another end abutting against said projection of said frame.

35. A matrix clamp as defined in claim 1, wherein said matrix band is composed of a corrosion-resistant metal.

36. A matrix clamp as defined in claim 1, wherein said matrix band is composed of a corrosion-resistant synthetic plastic material.

37. A matrix clamp as defined in claim 1, wherein said matrix band is formed as a one-piece integral element.

38. A matrix clamp as defined in claim 1, wherein said matrix band is formed as band article.

* * * * *